US012589018B2

(12) United States Patent
Heller

(10) Patent No.: US 12,589,018 B2
(45) Date of Patent: Mar. 31, 2026

(54) LUMBAR SUPPORT BELT WITH RIGID OUTER BELT

(71) Applicant: Brian Heller, Edgewater, NJ (US)

(72) Inventor: Brian Heller, Edgewater, NJ (US)

( * ) Notice: Subject to any disclaimer, the term of this patent is extended or adjusted under 35 U.S.C. 154(b) by 322 days.

(21) Appl. No.: 18/181,180

(22) Filed: Mar. 9, 2023

(65) Prior Publication Data

US 2024/0299199 A1    Sep. 12, 2024

(51) Int. Cl.
*A61F 5/02* (2006.01)
*A45F 3/14* (2006.01)
*A45F 5/00* (2006.01)

(52) U.S. Cl.
CPC ................ *A61F 5/028* (2013.01); *A45F 3/14* (2013.01); *A45F 2003/144* (2013.01); *A45F 5/1575* (2025.01)

(58) Field of Classification Search
CPC ...... A61F 5/02; A61F 5/028; A45F 2003/144; A45F 3/14; A45F 5/1575
See application file for complete search history.

(56) References Cited

U.S. PATENT DOCUMENTS

| | | | | | |
|---|---|---|---|---|---|
| 3,096,760 | A | * | 7/1963 | Nelkin | A61F 5/028 128/95.1 |
| 5,388,274 | A | | 2/1995 | Glover et al. | |

| | | | | | |
|---|---|---|---|---|---|
| 5,413,262 | A | * | 5/1995 | Dewire | A41F 9/002 224/675 |
| 5,464,136 | A | | 11/1995 | Eddy | |
| 5,497,923 | A | * | 3/1996 | Pearson | A41F 9/002 224/648 |
| 7,762,440 | B2 | * | 7/2010 | Cook | A45F 5/021 224/660 |
| 8,057,417 | B2 | | 11/2011 | Imai | |

FOREIGN PATENT DOCUMENTS

GB          2342589 B          9/2002
WO       2020188441 A1       3/2020

* cited by examiner

*Primary Examiner* — Keri J Nelson
(74) *Attorney, Agent, or Firm* — WELSH FLAXMAN & GITLER LLC

(57)          ABSTRACT

A lumbar support belt to be worn by a user includes an inner support belt having an inner surface adapted to contact the user when worn and an outer surface. The inner support belt having opposed free ends and an elongated section with a therebetween with a center. The lumbar support belt further including a rigid outer belt formed in two sections which are adjustable in length and attached to the outer surface of the inner support belt and an elastic reinforcement assembly secured to the outer surface of the inner support belt located at the center of the elongated section. The rigid outer belt cooperates with the elastic reinforcement assembly to actively expand the elastic reinforcement assembly when the rigid outer belt is secured around the user and the two sections are connected to one another by a buckle to provide concentrated lumbar support.

15 Claims, 7 Drawing Sheets

LUMBAR SUPPORT BELT WITH RIGID OUTER BELT

BACKGROUND OF THE INVENTION

1. Field of the Invention

This invention relates to a lumbar support which includes a rigid belt for support tools and equipment. More particularly, the invention relates to a lumbar support which can be secured around a user's lower back to assist in preventing lower back injuries and includes a rigid belt for supporting gear carried by first responders such as law enforcement officers, paramedics, emergency medical technicians, and firefighters, as well as any blue collar worker who wears a tool belt.

2. Description of the Related Art

The human spine is susceptible to a variety of injuries and disorders, particularly in the lower back (lumbar) region. Many people experience lower back pain, and it is a common cause of lost workdays and disability. A lumbar support belt is a device worn around the waist that provides support and stability to the lower back, helping to reduce pain and improve posture while people conduct heavy physical activities. Properly positioned lumbar support belts assist in reducing the pain felt by the wearer. Additionally, they function to hold the user in a proper position while conducting activities, in particular, they function to the support the lumbar region and the abdominal region of a user.

SUMMARY OF THE INVENTION

It is, therefore, an object of the present invention to provide a lumbar support belt to be worn by a user. The lumbar support belt includes an inner support belt having an inner surface adapted to contact the user when worn and an outer surface. The inner support belt has a first free end, an opposed second free end, and an elongated section therebetween with a center. The first free end and the opposed second free end are attachable to each other. The lumbar support belt also includes a rigid outer belt having a first section which is adjustable in length and attached to the outer surface of the inner support belt. The rigid outer belt also includes a second section which is adjustable in length and attached to the outer surface of the inner support belt spaced from the first section. An elastic reinforcement assembly is located at the center of the elongated section which is secured to the outer surface of the inner support belt. The rigid outer belt cooperates with the elastic reinforcement assembly to actively expand the elastic reinforcement assembly when the rigid outer belt is secured around the user and the first and second sections are connected to one another.

It is also an object of the present invention to provide a lumbar support belt wherein the inner support belt includes spaced hook or loop sections on the inner surface thereof located at the center, the first free end, and the opposed second free end.

It is also an object of the present invention to provide a lumbar support belt wherein the rigid outer belt includes a buckle to connect the first and sections of the rigid outer support belt together.

It is also an object of the present invention to provide a lumbar support belt wherein the elastic reinforcement assembly includes a first side located on one side of the center of the inner support belt and a second side located on an opposite side of the center of the inner support belt.

It is also an object of the present invention to provide a lumbar support belt wherein the first section of the rigid outer belt is connected to the first side of the elastic reinforcement assembly and the second section of the rigid outer belt is connected to the second side of the elastic reinforcement assembly.

It is also an object of the present invention to provide a lumbar support belt wherein the first section of the rigid outer belt is connected to the elastic reinforcement assembly by a first rigid ring and the second section of the rigid outer belt is connected to the second side of the elastic reinforcement assembly by a second rigid ring.

It is also an object of the present invention to provide a lumbar support belt wherein the elastic reinforcement assembly includes at least one elastic strap folded over to form a V-pattern creating a base on the first side of the elastic reinforcement assembly and at least one elastic strap folded over to form a V-pattern creating a base on the second side of the elastic reinforcement assembly.

It is also an object of the present invention to provide a lumbar support belt wherein the at least one elastic strap includes two straps.

It is also an object of the present invention to provide a lumbar support belt wherein the first section of the rigid belt includes a first end attached to the outer surface of the inner support belt and a free second end having a first portion of a buckle and the second section of the rigid belt includes a first end attached to the outer surface of the inner support belt and a free second end having a second portion of a buckle which can mate with the first portion of the buckle.

It is also an object of the present invention to provide a lumbar support belt wherein the first section extends from the attached first end of the first section toward the center of the inner support belt and passes through the first rigid ring and then reverses direction and continues toward the first free end of the inner support belt and the second section extends from the attached first end of the second section toward the center of the inner support belt and passes through the second rigid ring and then reverses direction and continues toward the opposed second free end of the inner support belt.

It is also an object of the present invention to provide a lumbar support belt wherein the free second end of the first section is folded and attached to itself by a hook-and-loop fastening system to adjustably secure the first portion of the buckle along the length of the first section and the free second end of the second section is folded and attached to itself by a hook-and-loop fastening system to adjustably secure the second portion of the buckle along the length of the second section.

It is also an object of the present invention to provide a lumbar support belt wherein the outer surface of the inner support belt includes hook or loop sections located at the first free end and the opposed second free end and the first and second sections of the rigid belt include hook or loop sections which cooperate with the hook or loop sections located at the first free end and the opposed second free end to secure the first and second sections of the rigid belt to the inner support belt.

It is yet another object of the present invention to provide a lumbar support belt, wherein the rigid outer belt is a duty belt supporting various gear, tools and equipment having a total weight of 35 pounds or less.

It is also an object of the present invention to provide a lumbar support belt wherein the inner support belt includes elastic panels and non-elastic panels connected to one another.

It is also an object of the present invention to provide a lumbar support belt wherein the inner support belt includes non-elastic panels connected to one another.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Figure 7:
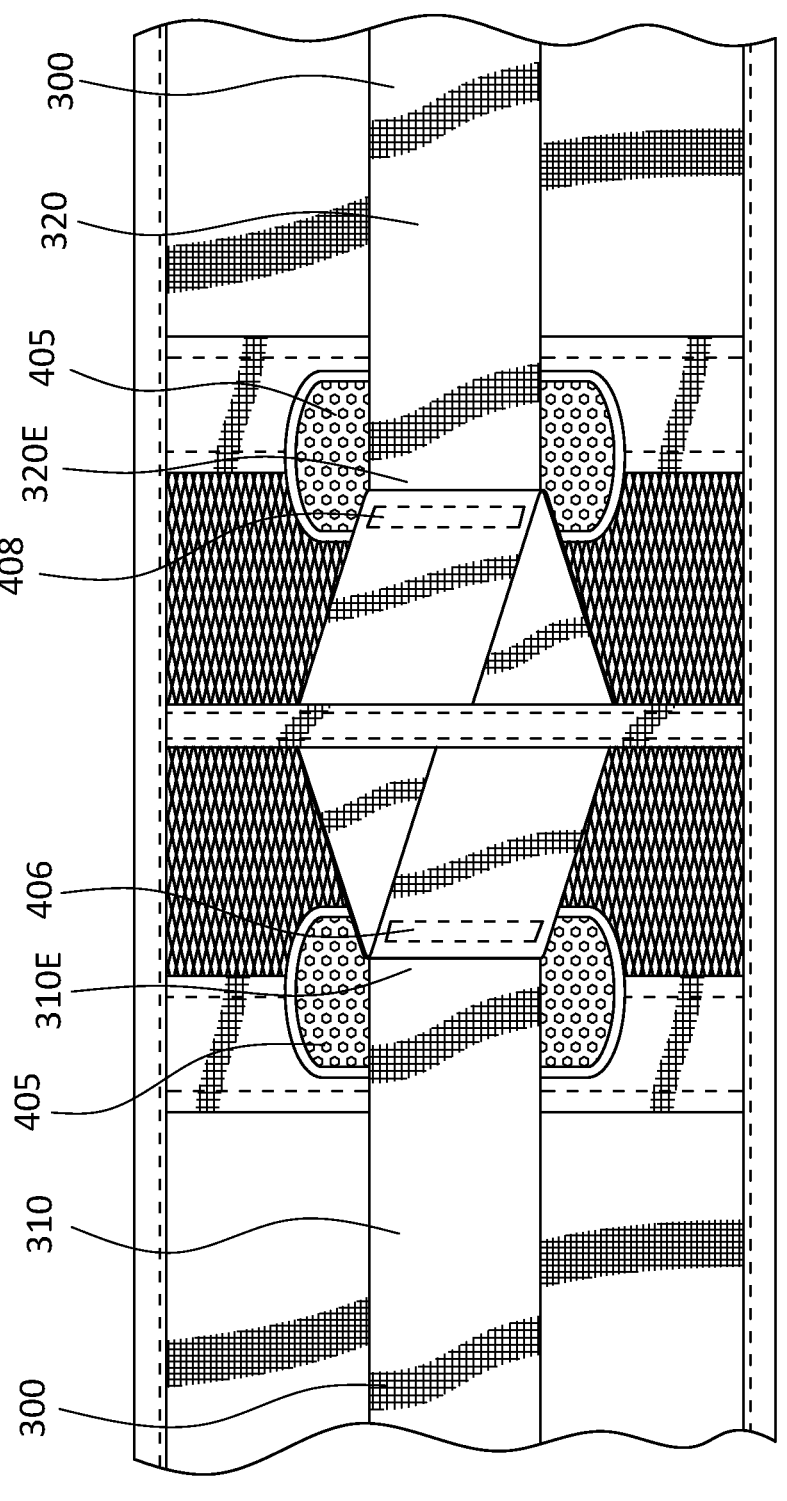
FIG. 7 is an enlarged view of the center panel of a second embodiment.

Referring to the various FIGS. 1 to 6, a lumbar support belt 100 of the present invention is shown. An alternative embodiment of the lumbar support belt 100A is shown in FIG. 7. The lumbar support belt 100 completely encircles the abdominal and lower lumbar regions of the body of a user when worn. The lumbar support belt 100 includes an inner support belt 200 having an inner surface 210 adapted to contact the user when worn and an outer surface 220. The inner support belt 200 also has opposed free ends 202 and 204 and an elongated section 206 with a center 205 therebetween. The opposed free ends 202 and 204 are attachable to each other via hook-and-loop fastening material as discussed below in greater detail. It is well appreciated that the hook and loop portions of hook-and-loop fastening material are interchangeable so long as there is maintained a pairing of the hooks with the loops or a pairing of the loops with the hooks. With this in mind, a hook portion or a loop portion may be generically referred to as a hook/loop fastener.

The lumbar support belt 100 further includes a rigid outer belt 300 formed in two sections which are adjustable in length and are attached to the outer surface 220 of the inner support belt 200. The lumbar support belt 100 also includes an elastic reinforcement assembly 400 secured to the outer surface 220 of the inner support belt 200 and located in the center 205 of the elongated section 206. The rigid outer belt 300 cooperates with the elastic reinforcement assembly 400 to expand the elastic reinforcement assembly 400 when the rigid outer belt 300 is secured around a user. Thus, the elastic reinforcement assembly 400 provides tensional support to the lumbar spine, that is, the elastic reinforcement assembly 400 is stretched to provide pressure to the lumbar spine.

When the lumbar support belt 100 is viewed from left to right along longitudinal axis X which is considered to be horizontal, the elongated section 206 is comprised of five horizontal panels; that is, a first panel 101, a second panel 102, a third panel 103, a fourth panel 104, and a fifth panel 105 which wrap around a user's waist when worn. As shown the lumbar support belt 100 includes an upper edge 111 and a lower edge 112. However, this is for illustration purposes only as the lumbar support belt 100 is symmetrical and can be worn such that lower edge 112 is located above upper edge 111. The first panel 101, the third panel 103, and the fifth panel 105 are made from a non-elastic breathable material, preferably foam mesh material and the second panel 102 and the fourth panel 104 are preferably made from an elastic material, such as twill woven elastic, but may be made from non-elastic materials, such as woven fabric.

The first panel 101 and the second panel 102 are sewn together by a first vertical strap 110. The second panel 102 and the third panel 103 are sewn together by a second vertical strap 120. The third panel 103 and the fourth panel 104 are sewn together by a third vertical strap 130. The fourth panel 104 and the fifth panel 105 are sewn together by a fourth vertical strap 140. The vertical straps are preferably made from nylon webbing. The vertical straps are located on both the inner surface 210 and the outer surface 220 of the inner support belt and the horizontal panels overlap adjacent panels prior to the vertical straps being sewn. Thus, a very strong connection between the horizontal panels is formed. The lumbar support belt 100 includes one more vertical strap, that is, a central vertical strap 150, which will be discussed in more detail below.

Each of the horizontal panels has an upper edge and lower edge, which respectively form part of the upper edge 111 and the lower edge 112. Accordingly, the first panel 101 includes an upper edge 101U and lower edge 101L, the second panel 102 includes an upper edge 102U and lower edge 102L, the third panel 103 includes an upper edge 103U and lower edge 103L, the fourth panel 104 includes an upper edge 104U and lower edge 104L, and the fifth panel 105 includes an upper edge 105U and lower edge 105L.

Starting centrally with the third panel 103, this is the widest panel from its upper edge 103U to its lower edge 103L and the upper and lower edges 103U, 103L are parallel to one another. On opposite sides of the third panel 103 are the second panel 102 and the fourth panel 104. The second and the fourth panels 102, 104 are the same width as the third panel 103 where they attach to the third panel 103 at the second and the third vertical straps 120, 130, respectively. However, the upper and lower edges 102U, 102L of the second panel 102 taper inwardly as they extend away from the third panel 103 toward first free end 202 of the inner support belt 200 and the upper and lower edges 104U, 104L of the fourth panel 104 taper inwardly as they extend away from the third panel 103 toward second free end 204 of the inner support belt 200. The fourth panel 104 tapers inwardly toward the fifth panel 105 where it is joined to the fifth panel 105 by the fourth vertical strap 140. The fifth panel 105 continues to taper inwardly from the fourth vertical strap 140 toward second free end 204 of the inner support belt 200. The second panel 102 tapers inwardly toward the first panel 101 where it is joined to the first panel 101 by the first vertical strap 110. The first panel 101 continues to taper inwardly from the first vertical strap 110 toward first free end 202 of the inner support belt 200.

Figure 1:
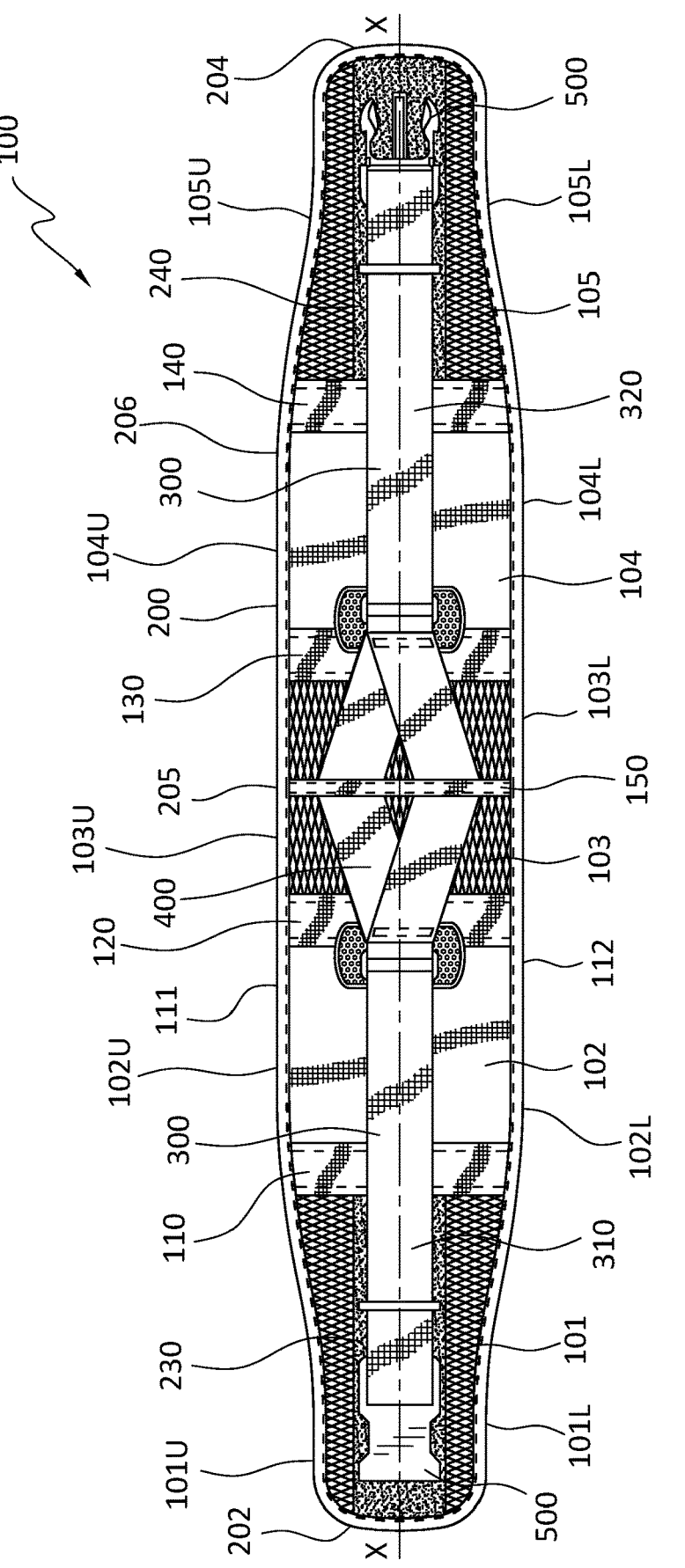
FIG. 1 is an outer rear view of the lumbar support belt of the present invention.
Figure 2:
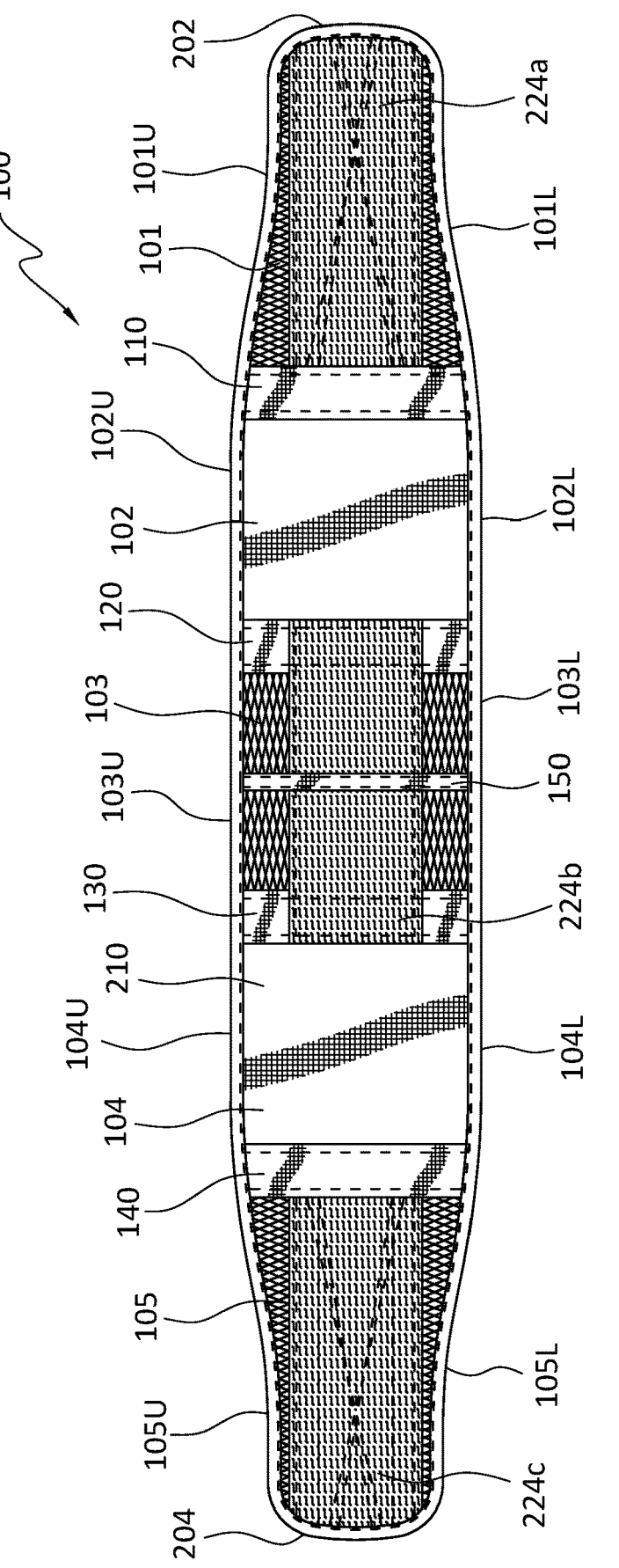
FIG. 2 is an inner view of the lumbar support belt of the present invention.
Figure 3:
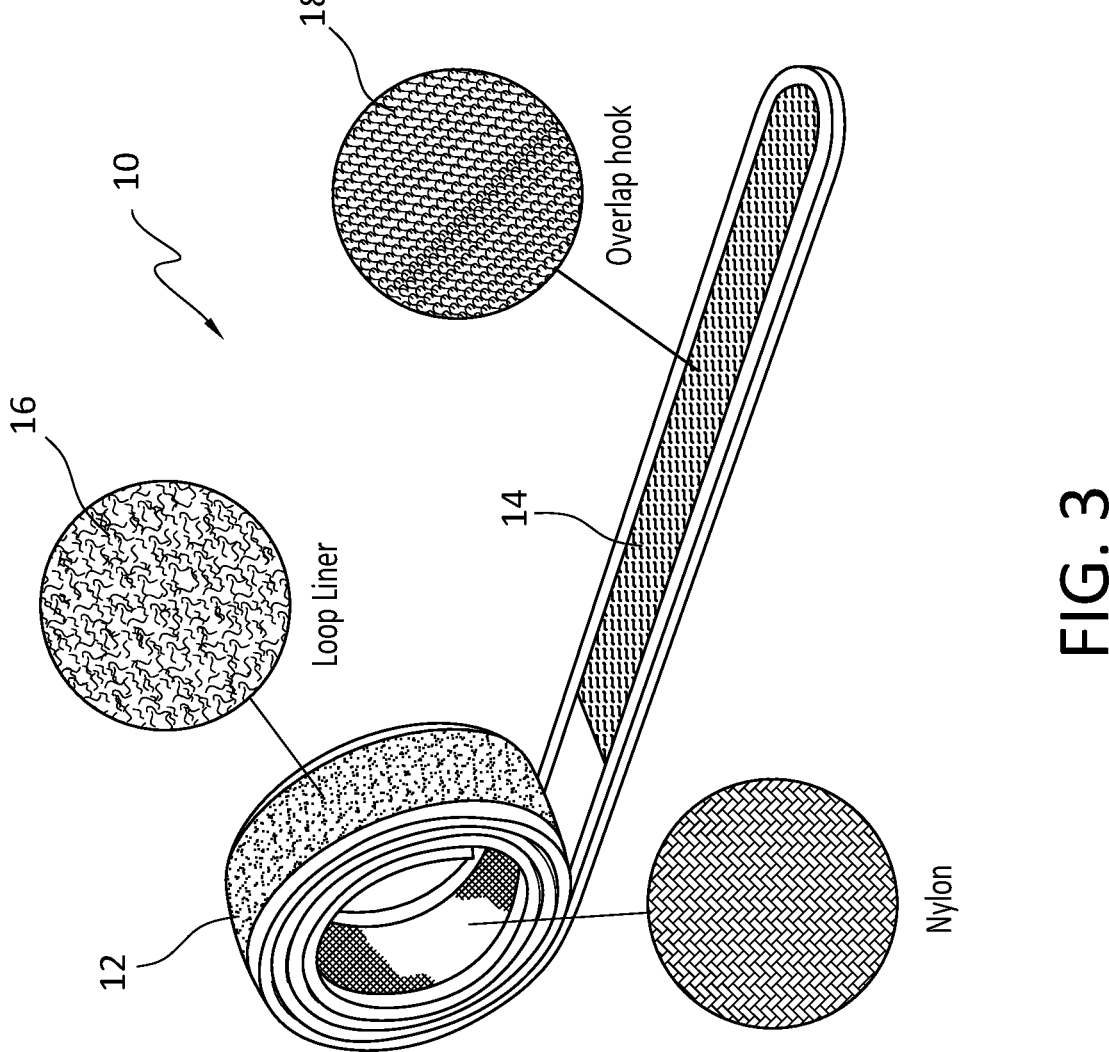
FIG. 3 is a perspective view of a hook-and-loop pants belt.

The inner surface 210 of the inner support belt 200 is designed to be used with a separate garment belt 10 which is passed through belt loops found about the waist of a garment worn by a user (not shown). The garment belt 10 is best shown in FIG. 3.

The garment belt 10 has an outer surface 12 covered with one portion, that is, either the hook portion or the loop portion, of a hook-and-loop fastening system. As shown in accordance with a disclosed embodiment, the outer surface 12 of garment belt 10 includes a loop liner 16. The garment belt 10 also includes an inner surface 14 with the hook portion 18 of a hook-and-loop fastening system covering a portion of the inner surface 14 adjacent one end thereof. In use, the loop liner 16 on the outer surface 12 of garment belt 10 is attach to the inner surface 210 of lumbar support belt 100 to assist in keeping the lumbar support belt 100 properly positioned about a user's lower back. Accordingly, the inner surface 210 of the inner support belt 200 includes spaced hook sections 224a, 224b, and 224c attached along the length of the inner surface 210 of the inner support belt 200, for example adjacent the ends and center of the inner support belt 200, which cooperate with the loop liner 16 on the outer surface 12 of the garment belt 10 to prevent the lumbar support belt 100 from moving up a user's body when properly position around a user. The hook sections 224a, 224b, and 224c are preferably sewn onto the inner surface of inner support belt 200. The hook section 224a starts proximate the first free end 202 of the inner support belt 200 and travels longitudinally along the length of the first panel 101 toward second free end 204 a distance of several inches where it meets the first vertical strap 110. The hook section 224c starts proximate the second free end 204 of the inner support belt 200 and travels longitudinally along the length of fifth panel 105 toward first free end 202 a distance of several inches where it meets the fourth vertical strap 140. The hook section 224b is located centrally along the length of the inner support belt 200 and is spaced equal distances from the hook sections 224a and 224c and is located on third panel 103.

The outer surface 220 of the inner support belt 200 includes a loop section 230 located on the first panel 101 and a loop section 240 located on the fifth panel 105. These loop sections 230, 240 are sewn on the first and fifth panels 101, 105 and correspond with the hook sections 224a and 224c. That is, the loop section 230 is located on the outer side of the first panel 101 opposite the hook section 224a located on the inner side of the first panel 101 and the loop section 240 is located on the outer side of the fifth panel 105 opposite the hook section 224c located on the inner side of the fifth panel 105. The hook section 224c can be attached to the loop section 230 or the hook section 224a can be attached to the loop section 240 to secure the inner support belt 200 about a user.

Figure 4:
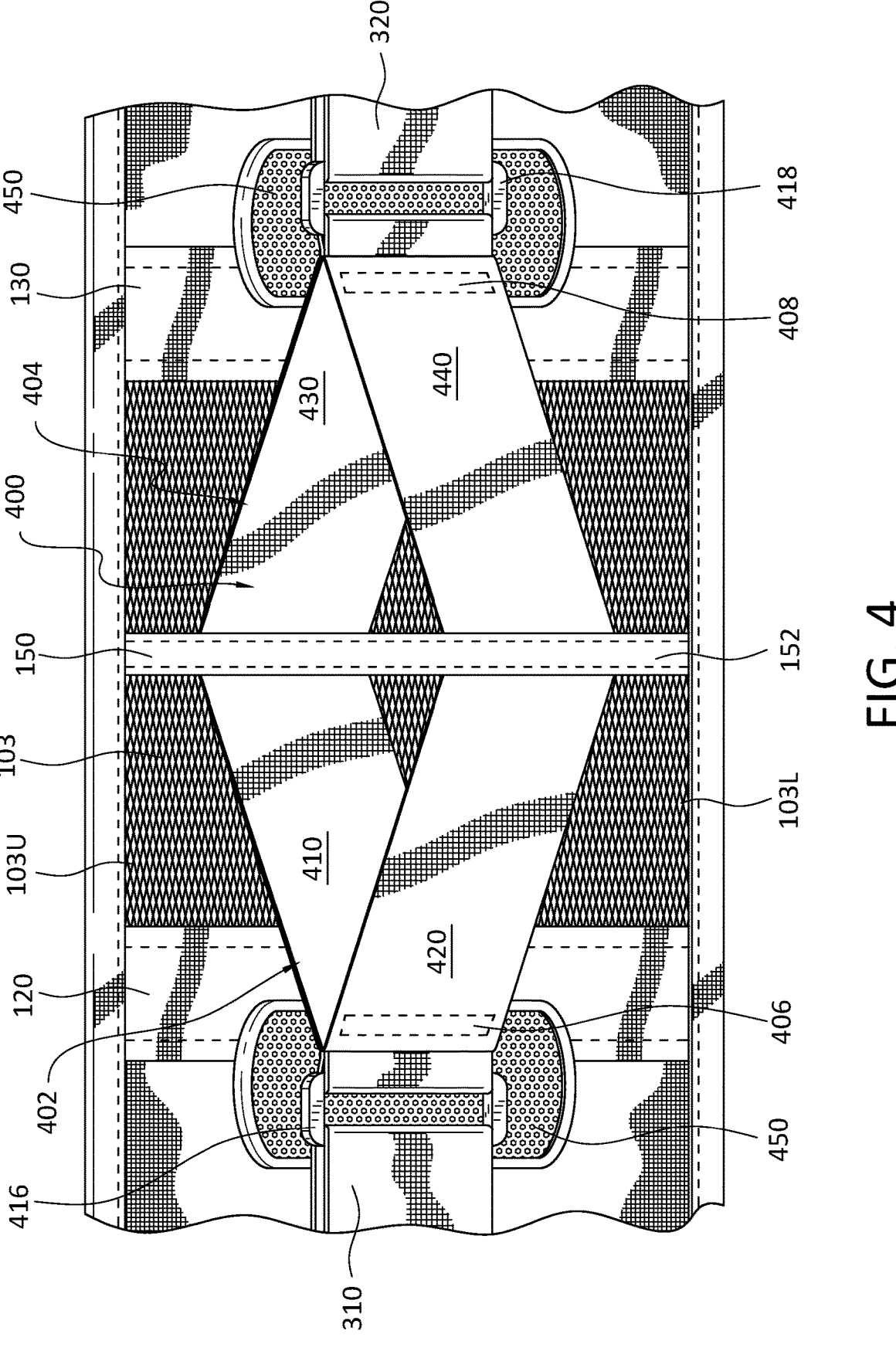
FIG. 4 is an enlarged view of the center panel shown in FIG. 1.
Figure 5:
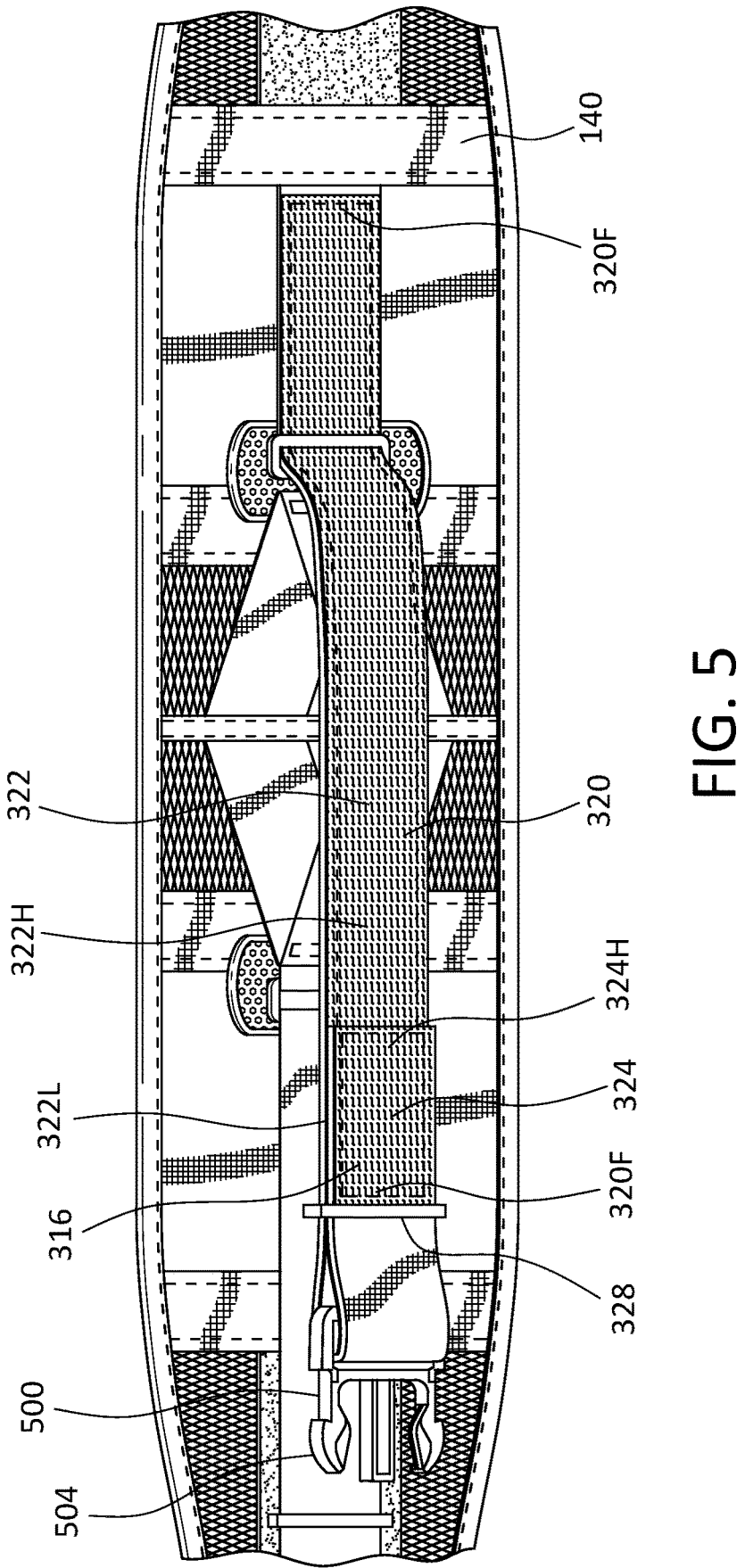
FIG. 5 is an enlarged view of the first section of the rigid outer belt.
Figure 6:
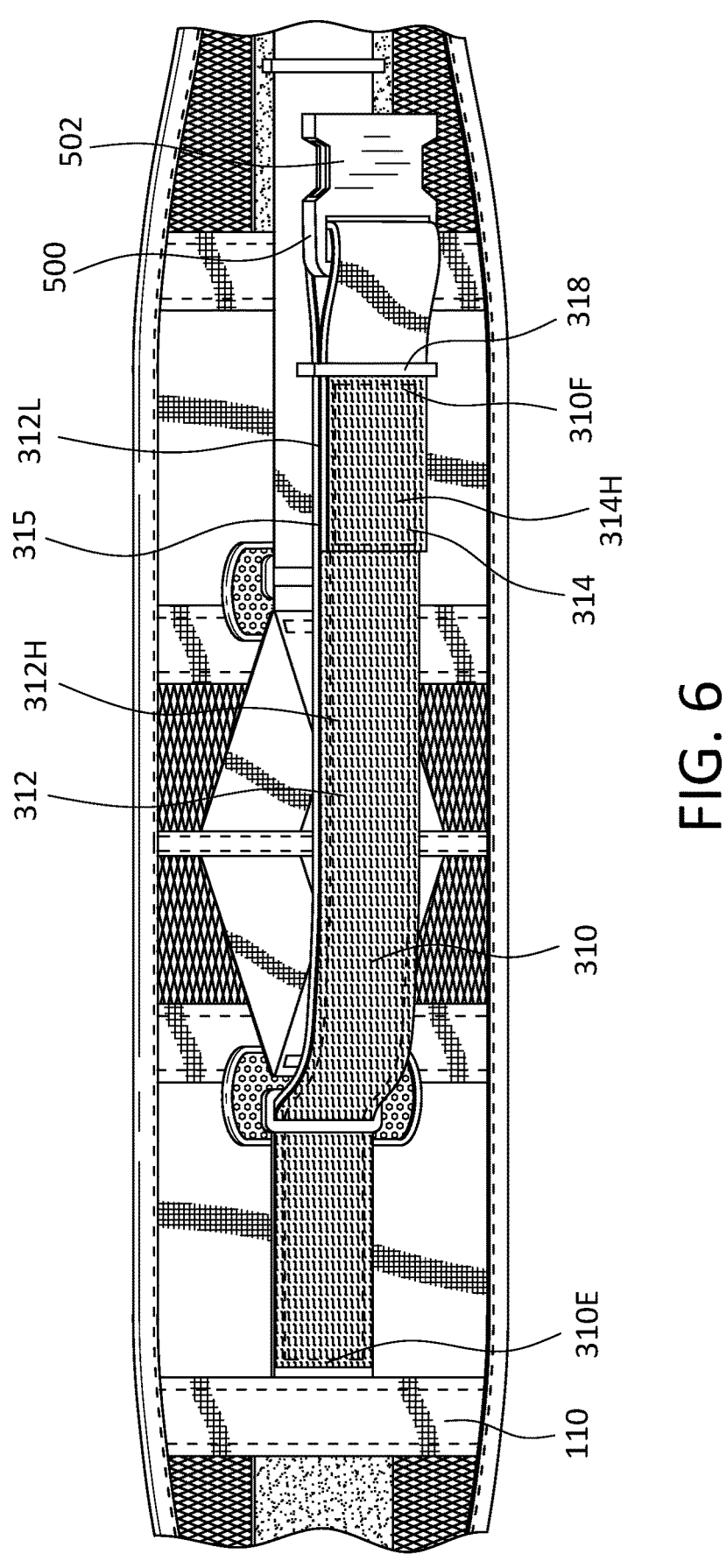
FIG. 6 is an enlarged view of the second section of the rigid outer belt.

As best illustrated in FIG. 4, the third panel 103, which is centrally located on the inner support belt 200, includes an elastic reinforcement assembly 400 secured to the outer surface of the inner support belt 200 by the central vertical strap 150 mentioned above. One side of the elastic reinforcement assembly 400 lies on a first side 152 of the central vertical strap 150 and includes legs 410 and 420 formed of one or more elastic straps 402. The other side of the elastic reinforcement assembly 400 lies on an opposite second side 154 of the central vertical strap 150 and includes legs 430) and 440 formed of one or more elastic straps 404. The elastic strap or straps 402 are folded over to form a V-pattern creating a base 406 of the V which is attached to a rigid ring 416 via an attachment loop 407. The rigid ring 416 can be made from metal or plastic. The legs 410 and 420 are secured to third panel 103 by the central vertical strap 150 which is sewn to both the inner surface 210) and outer surface 220 of the inner support belt 200. The elastic strap or straps 404 are folded over to form a V-pattern creating a base 408 of the V which is attached to a rigid ring 418 via an attachment loop 409. The rigid ring 418 can be made from metal or plastic. The legs 430 and 440 are secured to the third panel 103 by the central vertical strap 150 which is sewn to both the inner surface 210) and outer surface 220 of the inner support belt 200. At the base 406 and 408 a cushion 450 is secured under the rigid rings 416 and 418. Cushions 450 prevent the rigid rings 416, 418 from making direct contact with outer surface 220 of the inner support belt 200 providing additional comfort when the lumbar support belt 100 is worn.

Importantly the outer surface 220 of the inner support belt 200 includes a rigid outer belt 300 formed in a first section 310 and a second section 320, which function as duty belt when secured together via a buckle 500. Rigid means the sections 310 and 320 are not elastic in any direction and they do not bend when subjected to lateral forces directed from an edge thereof to an opposite edge thereof. Accordingly, the first and second sections 310 and 320 can support tools and/or equipment weighing over 30 pounds. The rigid outer belt 300 is designed like a duty belt to support tools and equipment having a total weight of 35 pounds or less. The rigid outer belt 300 is comprised of a non-elastic durable material which is rigid such that it does not flex laterally and is not as wide as any portion of the five horizontal panels of the inner support belt 200. Like duty belts, rigid outer belt 300 has a width of between 2 to 2¼ inches and can be made from ballistic nylon or heavy nylon/propylene. The rigid outer belt 300 primarily provides support for gear, such as first aid gear, radios, firearms, handcuffs, batons, flashlights, keys and various other tools or equipment needed by the user, but it also cooperates with the elastic reinforcement assembly 400 to provide additional back support. Since rigid outer belt 300 is rigid and non-elastic is functions to actively expand elastic reinforcement assembly 400 along the longitudinal axis X to provide concentrated lumbar support when properly adjusted for a user.

The first section 310 includes a first end 310E and a second end 310F. The first end 310E is attached to the outer surface 220 of the inner support belt 200 at and by the first vertical strap 110. The second section 320 includes a first end 320E and a second end 320F. The first end 320E is attached to the outer surface 220 of the inner support belt 200 at and by the fourth vertical strap 140. The length of the first section 310 and the second section 320 are effectively adjustable in length as portions of a buckle 500 can be positioned and locked at varying locations along the length thereof.

Beginning at the first end 310E, the first section 310 extends from the first vertical strap 110 toward the central vertical strap 150, passes through rigid ring 416 and then reverses direction and continues toward the first free end 202 of the inner support belt 200 where the second end 310F is folded and attached to itself by a hook-and-loop fastening system to secure a female portion 502 of the buckle 500 along the length of the first section 310.

Beginning at the first end 320E, the second section 320 extends from the fourth vertical strap 140 toward the central vertical strap 150, passes through rigid ring 418 and then reverses direction and continues toward the second free end 204 of the inner support belt 200 where the second end 320F is folded and attached to itself by a hook-and-loop fastening system to secure a male portion 504 of the buckle 500 along the length of the second section 320. The male portion 504 and the female portion 502 of the buckle 500 are joined together in a conventional manner such that the rigid outer belt 300 and elastic reinforcement assembly 400 completely encircle the abdominal and lower lumbar regions of the body of a user.

As briefly discussed above, the first section 310 of rigid outer belt 300 is effectively adjustable in length. The first section 310 includes a hook and loop assembly 315 to adjustably secure the female portion 502 of the buckle 500 to the first section 310 to thereby adjust the effective length of the first section 310. The first section 310 has a first side 312 having a hook section 312H running almost the length of the surface thereof except for the last three inches which includes loops section 312L covering the surface thereof. The opposite second side 314 of the first section 310 includes hook section 314H covering the surface at the free end 316. The first section 310 further includes a rigid ring 318 which can slide along the length thereof. To adjust the length of the first section 310 the position of the female portion 502 of the buckle 500 is moved along the length of the first section 310. Once the desired position of the female portion 502 of the buckle 500 along the length of the first section 310 has been determined, the first side 312 of the first section 310 is folded back upon itself and loops section 312L is secured to the hook section 312H to lock the female portion 502 of the buckle 500 in place and then rigid ring 318 is slid over the hook section 314H. The hook section 314H can be secured to the loop section 230 to further support the first section 310 of the rigid outer belt 300 in place. This prevents the rigid outer belt 300 from sagging when weighted with tools and equipment.

The second section 320 of the rigid outer belt 300 is also effectively adjustable in length. The second section 320 includes a hook and loop assembly 317 to adjustably secure the male portion 504 of the buckle 500 to the second section 320 to thereby adjust the length of the second section 320. The second section 320 has a first side 322 having a hook section 322H running almost the length of the surface thereof except for the last three inches which includes a loops section 322L covering the surface thereof. The opposite second side 324 of the second section 320 includes hook section 324H covering the surface at the free end 319. The second section 320 further includes a rigid ring 328 which can slide along the length thereof. To adjust the length of the second section 320, the position of the male portion 504 of the buckle 500 is moved along the length of the second section 320. Once the desired position of the male portion 504 of the buckle 500 along the length of section 320 has been determined the first side 322 of the second section 320 is folded back upon itself and the loops section 322L is secured to the hook section 322H to lock the male portion 504 of the buckle 500 in place and then the rigid ring 328 is slid over the hook section 324H. The hook section 324H can be secured to loops section 240 to further support the second section 320 of the rigid outer belt 300 in place. This prevents the rigid outer belt 300 from sagging when weighted with tools and/or equipment.

The length of the rigid outer belt 300 is adjustable to fit users of different sizes but also such that the elastic reinforcement assembly can be stretched under tension to provide increased support to the user lumbar spine.

In use, the inner surface 210 of the inner support belt 200 is tightly secured around a user's lower back and waist by attaching hook section 224a at first free end 202 to loops section 240 at second free end 204 or attaching hook section

224c at second free end 204 to loop section 230 at first free end 202. If a user is wearing the garment belt 10 covered with the loop liner 16, hook sections 224a, 224b and 224c will be secured thereto. Next after the first and second sections 310 and 320 have been adjusted to the proper length the free ends of rigid outer belt 300 are pull around the outer surface 220 of the inner support belt 200 and the male portion 504 of the buckle 500 is secured to the female portion 502 of the buckle 500 while securing hook section 314H to loop section 230 and hook section 324H to loop section 240.

An alternate embodiment of the rigid outer belt 300 and elastic reinforcement assembly 400 are shown in FIG. 7. In this embodiment the first section 310 of rigid outer belt 300 is directly connected to the base 406 by sewing the base 406 to an end 310E of the first section 310 and cushion 450 and the second section 320 of rigid outer belt 300 is directly connected to the base 408 by sewing the base 408 to an end 320E of the second section 320 and cushion 450.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A lumbar support belt to be worn by a user comprising:
an inner support belt having an inner surface adapted to contact the user when worn and an outer surface, the inner support belt having a first free end, an opposed second free end, and an elongated section therebetween with a center having a midline, wherein the first free end and the opposed second free end are attachable to each other;
a rigid outer belt including a first section which is adjustable in length and attached to the outer surface of the inner support belt and a second section which is adjustable in length and attached to the outer surface of the inner support belt spaced from the first section;
and an elastic reinforcement assembly located at the center of the elongated section which is secured to the outer surface at the midline of the inner support belt is configured to expand and provide concentrated lumbar support;
wherein the rigid outer belt cooperates with the elastic reinforcement assembly to actively expand the elastic reinforcement assembly when the rigid outer belt is secured around the user and the first and second sections are connected to one another.

2. The lumbar support belt of claim 1, wherein the inner support belt includes spaced hook or loop sections on the inner surface thereof located at the center, the first free end, and the opposed second free end.

3. The lumbar support belt of claim 1, wherein the rigid outer belt includes a buckle to connect the first and second sections of the rigid outer belt together.

4. The lumbar support belt of claim 1, wherein the elastic reinforcement assembly includes a first side located on one side of the center of the inner support belt and extending from the center of the inner support belt and a second side located on an opposite side of the center of the inner support belt and extending from the center of the inner support belt.

5. The lumbar support belt of claim 4, wherein the first section of the rigid outer belt is connected to the first side of the elastic reinforcement assembly and the second section of the rigid outer belt is connected to the second side of the elastic reinforcement assembly.

6. The lumbar support belt of claim 5, wherein the first section of the rigid outer belt is connected to the elastic reinforcement assembly by a first rigid ring and the second section of the rigid outer belt is connected to the second side of the elastic reinforcement assembly by a second rigid ring.

7. The lumbar support belt of claim 6, wherein the first section of the rigid outer belt includes a first end attached to the outer surface of the inner support belt and a free second end having a first portion of a buckle and the second section of the rigid outer belt includes a first end attached to the outer surface of the inner support belt and a free second end having a second portion of a buckle which can mate with the first portion of the buckle.

8. The lumbar support belt of claim 7, wherein the first section extends from the attached first end of the first section toward the center of the inner support belt and passes through the first rigid ring and then reverses direction and continues toward the first free end of the inner support belt and the second section extends from the attached first end of the second section toward the center of the inner support belt and passes through the second rigid ring and then reverses direction and continues toward the opposed second free end of the inner support belt.

9. The lumbar support belt of claim 7, wherein the free second end of the first section is folded and attached to itself by a hook-and-loop fastening system to adjustably secure the first portion of the buckle along the length of the first section and the free second end of the second section is folded and attached to itself by a hook-and-loop fastening system to adjustably secure the second portion of the buckle along the length of the second section.

10. The lumbar support belt of claim 4, wherein the elastic reinforcement assembly includes at least one elastic strap folded over to form a V-pattern creating a base on the first side of the elastic reinforcement assembly and at least one elastic strap folded over to form a V-pattern creating a base on the second side of the elastic reinforcement assembly.

11. The lumbar support belt of claim 10, wherein the at least one elastic strap on the first side of the elastic reinforcement assembly includes two straps and the at least one elastic strap on the second side of the elastic reinforcement assembly includes two straps.

12. The lumbar support belt of claim 1, wherein the outer surface of the inner support belt includes hook or loop sections located at the first free end and the opposed second free end and the first and second sections of the rigid outer belt include hook or loop sections which cooperate with the hook or loop sections located at the first free end and the opposed second free end to secure the first and second sections of the rigid outer belt to the inner support belt.

13. The lumbar support belt of claim 1, wherein the rigid outer belt is a duty belt configured to support various gear, tools and equipment having a total weight of 35 pounds or less.

14. The lumbar support belt of claim 1, wherein the inner support belt includes elastic panels and non-elastic panels connected to one another.

15. The lumbar support belt of claim 1, wherein the inner support belt includes non-elastic panels connected to one another.

* * * * *